(12) United States Patent
Maxwell et al.

(10) Patent No.: US 6,514,206 B2
(45) Date of Patent: Feb. 4, 2003

(54) SIMULTANEOUS FUNDAMENTAL AND HARMONIC ULTRASONIC IMAGING

(75) Inventors: Douglas R. Maxwell, Woodinville, WA (US); James R. Jago, Seattle, WA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/802,491

(22) Filed: Mar. 9, 2001

(65) Prior Publication Data
US 2002/0128555 A1 Sep. 12, 2002

(51) Int. Cl.[7] ................................................ A61B 8/00
(52) U.S. Cl. ........................................ 600/443; 600/447
(58) Field of Search ......................... 600/437, 440–447, 600/453–458; 73/625, 626; 367/7, 11, 138

(56) References Cited

U.S. PATENT DOCUMENTS

| 5,318,033 A | 6/1994 | Savord |
| 5,526,816 A | 6/1996 | Arditi |
| 5,577,505 A | 11/1996 | Brock-Fisher et al. |
| 5,623,928 A | 4/1997 | Wright et al. |
| 5,632,277 A | 5/1997 | Chapman et al. |
| 5,667,373 A | 9/1997 | Wright et al. |
| 5,706,819 A | 1/1998 | Hwang et al. |
| 5,897,500 A | 4/1999 | Zhao |
| 5,902,243 A | 5/1999 | Holley et al. |
| 5,961,460 A * | 10/1999 | Guracar et al. ............. 600/440 |
| 6,048,316 A | 4/2000 | Zhao et al. |
| 6,050,942 A * | 4/2000 | Rust et al. .................. 600/437 |
| 6,117,082 A | 9/2000 | Bradley et al. |
| 6,193,662 B1 | 2/2001 | Hwang |
| 6,231,511 B1 * | 5/2001 | Bae ............................ 600/447 |
| 6,454,714 B1 * | 9/2002 | Ng et al. .................... 600/443 |

* cited by examiner

Primary Examiner—Marvin M. Lateef
Assistant Examiner—Ali M. Imam
(74) Attorney, Agent, or Firm—W. Brinton Yorks, Jr.

(57) ABSTRACT

An ultrasonic diagnostic imaging system and method are described for performing fundamental frequency and second harmonic frequency imaging simultaneously. Transmit bursts are employed which include a first waveform component optimized for fundamental imaging and a second waveform component optimized for harmonic imaging. The first waveform component may be centered in the transducer passband, and the second waveform component may be located on the opposite side of the center of the transducer passband from its second harmonic frequency, for instance. Echoes received from the bursts are separated into fundamental and harmonic components and used to form separate fundamental and harmonic images or blended fundamental/harmonic images.

28 Claims, 5 Drawing Sheets

SIMULTANEOUS FUNDAMENTAL AND HARMONIC ULTRASONIC IMAGING

This invention relates to ultrasonic diagnostic imaging systems and, in particular, to ultrasonic diagnostic imaging systems which utilize both fundamental and harmonic ultrasonic signals for imaging.

In ultrasonic harmonic imaging, two dimensional (2D) or three dimensional (3D) images are formed by transmitting ultrasound at one frequency (or range of frequencies) and receiving at this frequency and higher harmonics of the transmit frequency. These harmonic signals are generated either by scattering from bubbles (harmonic contrast) as described in U.S. Pat. No. 5,879,303 or by non-linear propagation in tissue (tissue harmonic imaging, or THI) as described in U.S. Pat. No. 5,833,613. Typically, receive beams are formed only from the second harmonic echo signals, with the transmitted (or "fundamental") echo signals being removed either by filtering or by cancellation techniques such as pulse inversion. See U.S. Pat. No. 5,951,478. For THI, adequate removal of the fundamental signal is essential for the improvements in clutter suppression and contrast resolution which are typically seen.

In order to receive sufficient 2nd harmonic signal energy to form an high quality image, the transmitted signal frequency is typically lowered to approximately $\frac{2}{3}$ of the "nominal" center frequency of the scanhead. This is illustrated in FIG. 1, where Tx illustrates a transmit band, Rx illustrates a 2nd harmonic receive band, and the passband 14 of the scanhead transducer has a nominal center frequency of $F_c$. This means that the 2nd harmonic signal is now at $\frac{4}{3}$ of the nominal center frequency and hence still within the bandwidth of a typical transducer. For example, for a nominally 3 MHz transducer center frequency operating in harmonic mode the transmit frequency might be 2 MHz with the 2nd harmonic at 4 MHz. Although the transmitted (or fundamental) frequencies can be partially removed from the received beam by filtering techniques, pulse inversion, in which two pulses of opposite polarity are transmitted sequentially and the rf echo signals received from each pulse are summed, is much more effective, at least in situations of comparatively slow target movement. The major disadvantage of pulse inversion is the factor of two decrease in frame rate that is incurred.

Under some circumstances it may be of interest to image with both the 2nd harmonic signal and the fundamental signal which would normally be discarded in harmonica imaging. For example, two of the limitations of THI are poor near-field imaging (before non-linear propagation has had a chance to generate a significant 2nd harmonic response) and poor penetration, because the 2nd harmonic echo is highly attenuated as compared to the fundamental echo signal. One option for addressing this problem is to image with the fundamental signal in the near and far fields while imaging the 2nd harmonic in the mid-field. See, for example, U.S. Pat. No. 6,283,919 which teaches the formation of ultrasonic images which are a blend of fundamental and harmonic signals. Fundamental signals can also be combined with 2nd harmonic signals to provide speckle reduction through frequency compounding.

One of the main disadvantages with imaging the fundamental signal from a typical harmonic imaging transmit burst is that the fundamental is typically of lower frequency and bandwidth than that used for "conventional" fundamental-only imaging, as shown in FIG. 1, resulting in poor lateral and axial resolution. Thus, it would be desirable to transmit bursts which are optimized for both fundamental and harmonic performance to realize the full benefits of the respective imaging modes, and to do so with little or no penalty in frame rate.

In accordance with the principles of the present invention, a method is described for imaging both conventional fundamental and 2nd harmonic signals with little or no frame rate loss. In a preferred embodiment the inventive method includes transmitting an ultrasound wave which incorporates two transmit waveforms, one optimized for fundamental imaging and another optimized for THI imaging. In accordance with a further aspect of the present invention, two sequential transmit bursts of this form are used, with the same THI waveform but different fundamental waveforms. When the depth-corresponding echoes from the two bursts are summed, the optimized fundamental signals cancel, leaving a distinct and optimized THI echo and its transmitted fundamental, which may be processed in the usual manner for THI imaging. When the echoes from the two bursts are subtracted, the optimized fundamental signals are preserved as the THI signals are cancelled. These signals may be processed in the usual manner for fundamental imaging. Since the two signals are available simultaneously, images which are a blend of optimized fundamental and harmonic signals can be produced.

Figure 2A:
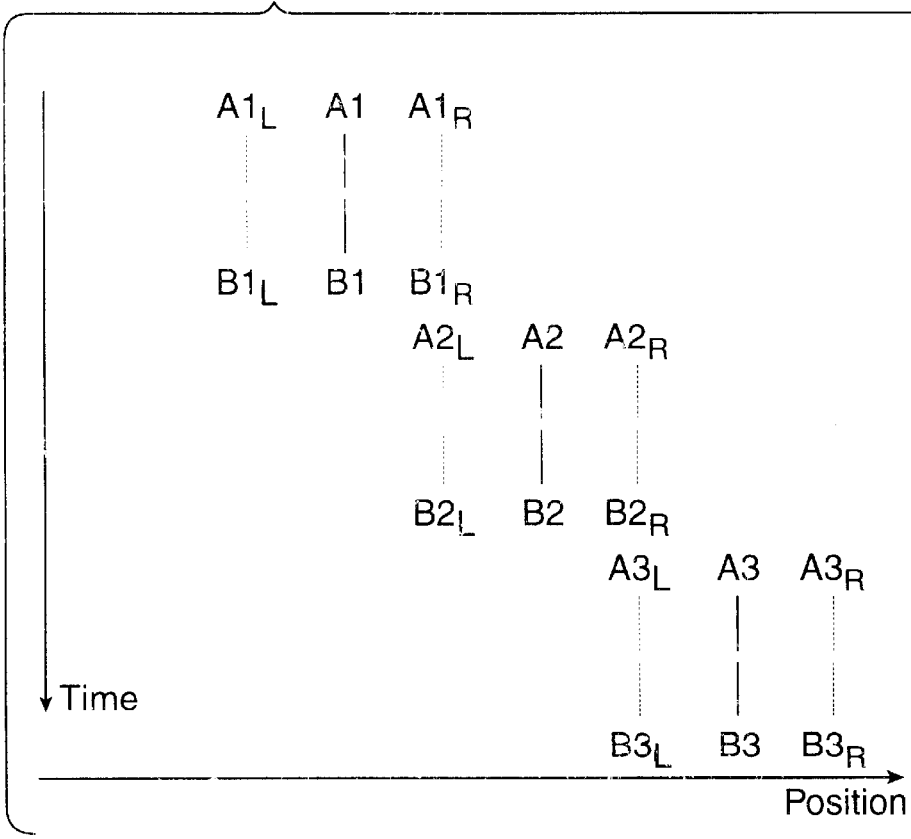
FIGS. 2a–2c illustrate the use of multiline reception and rf interpolation to form image lines from successive THI and conventional transmit bursts.
Figure 2B:
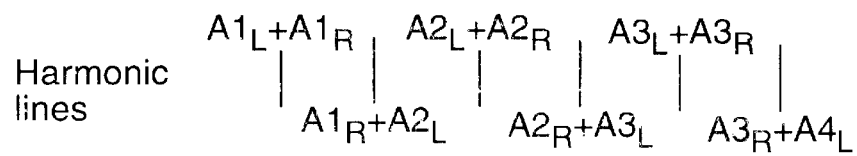
Figure 2C:
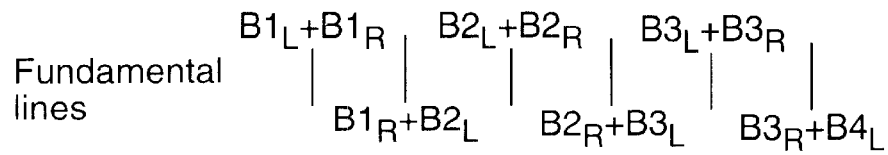

One approach to simultaneous fundamental and harmonic imaging is to transmit sequentially a harmonic burst and a conventional burst, and use the echoes resulting from each transmit burst to generate 2nd harmonic and fundamental image lines respectively. However this costs a factor of two in frame rate, since n transmit bursts for the n lines of the harmonic image must be transmitted and N transmit bursts for the N lines of the fundamental image must be transmitted. One way of potentially overcoming this frame rate reduction is to use multiline (or combined rf interpolation and multiline) to allow the transmit line density to be reduced by a factor of two. This approach is shown in FIG. 2 and forms harmonic and fundamental image lines by a combination of multiline reception and rf interpolation. In FIG. 2a A1, A2 and A3 indicate the times of transmission (by their vertical location) and spatial locations (by their horizontal position) of transmit beams optimized for harmonic imaging. Multiline reception is employed to receive two scanlines for each transmit beam, one to the left of the center of the transmit beam and one to the right of the center of the transmit beam. For instance, the transmission of beam A1 results in the reception of left and right scanlines $A1_L$ and $A1_R$. In a similar manner B1, B2 and B3 indicate the times of transmission and spatial locations of transmit beams optimized for fundamental imaging. Multiline reception is used for the fundamental signals also. For instance, the transmission of beam B1 results in the reception of left and right scanlines $B1_L$ and $B1_R$. The scanlines from the harmonic transmit beams are interpolated (summed and weighted) as shown in FIG. 2b to form harmonic image lines. This interpolation helps to reduce or eliminate beam steering, spatial sampling, and other distortion artifacts that would otherwise affect multiline beams, as known in the art. The first harmonic image line is the sum of $A1_L+A1_R$, which produces an image line at the spatial location of the A1 transmit aperture. The next harmonic image line is the sum of $A1_R+A2_L$, which produces an image line at the spatial location of the receive apertures of scanlines $A1_R$ and $A2_L$. The rest of the harmonic image lines are produced by repeating this combinational sequence. The image lines are seen to be alternating combinations of temporally identical and temporally different receive beams, which can produce an artifact in the presence of motion. This motion artifact can be overcome by the uniform use of temporally different scanline combinations as explained in U.S. patent [application Ser. No. 09/252,053]. The fundamental image lines are produced by interpolation in the same combinational sequence as shown in FIG. 2c. Note that to minimize spatial artifacts the transmit line density must still be high enough to ensure that the transmit lines are adequately sampled in space. In this embodiment the use of 2:1 multiline and rf interpolation enables two images, one harmonic and one fundamental, to be scanned in the same time required to scan a single image without multiline reception.

Figure 3A:
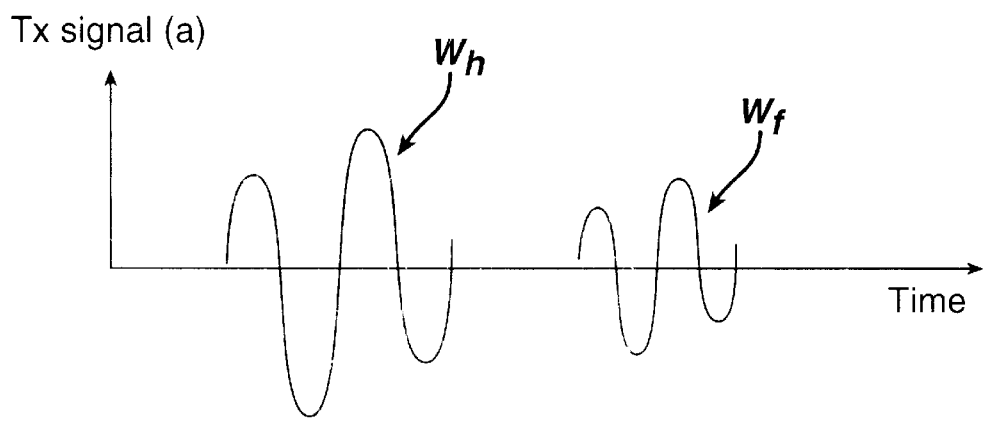
FIGS. 3a and 3b illustrate transmit bursts containing waveforms for both fundamental and harmonic imaging in accordance with a preferred embodiment of the present invention.

In accordance with the principles of the present invention, signals are acquired for both conventional fundamental and 2nd harmonic imaging with no frame rate loss, wherein both the fundamental and 2nd harmonic signal characteristics can be independently optimized and which do not suffer from the limitations (motion artifacts, etc.) of the previously described approach. This is accomplished by transmitting a burst which incorporates two transmit waveforms, one for conventional fundamental imaging (with a center frequency preferably close to the center frequency $F_c$ of the scanhead) and one for THI imaging (with a center frequency preferably close to ⅔ of the center frequency of the scanhead) as shown in FIG. 3a, where $W_h$ is the optimized harmonic waveform and $W_f$ is the optimized fundamental waveform. The harmonic waveform $W_h$ may be of a greater amplitude than the fundamental waveform to account for the attenuation and lesser intensity of harmonic signals. Note that the transmit waveforms may be time simultaneous and transmitted as a composite of the two waveforms, but are shown as separated in time in FIG. 3a for clarity.

In accordance with a further aspect of the present invention, transmission is performed as two sequential bursts separated by a pulse repetition interval (PRI). Both of the transmit bursts incorporate transmit waveforms for conventional fundamental imaging and THI imaging as described above, with the sequential bursts being identical except that the conventional waveform $W_f$ is differently modulated from burst to burst. The burst-to-burst modulation of the conventional waveform can be a phase difference or an amplitude difference, but is an inverted waveform $W_f{'}$ as shown in the second burst of FIG. 3b. FIG. 4 shows the frequency content of the received signals arising from either of the transmit bursts shown in FIG. 3a or 3b, after propagation through tissue and the scanhead. Band 102 is the band of signals resulting from fundamental reception of echoes from the $W_h$ transmit waveform, band 104 is the band of signals resulting from fundamental reception of echoes from the fundamental waveform $W_f$ transmitted at the scanhead center frequency $F_c$, and band 106 is the band of 2nd harmonic signals resulting from transmission of the $W_h$ waveform. Note that the conventional transmit waveform $W_f$ also generates 2nd harmonic signals in a band 108, but the amplitude of these signals is low because of the low sensitivity of the scanhead at this high frequency ($2 \times F_c$).

Figure 1:
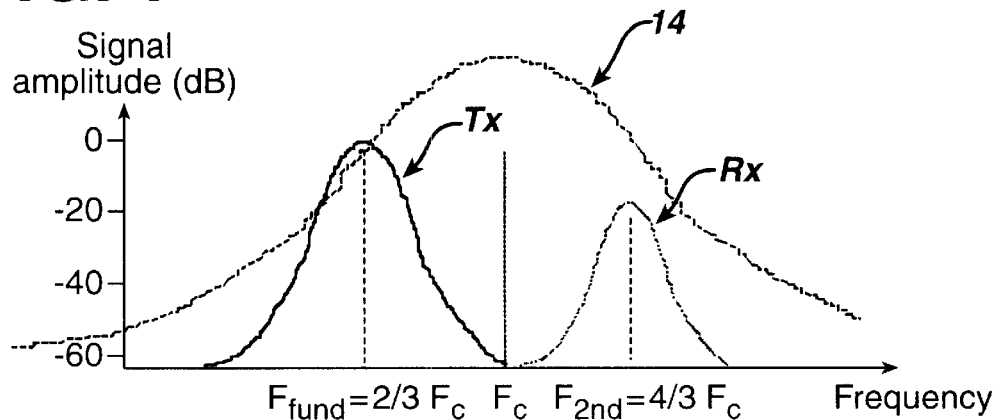
FIG. 1 illustrates a scanhead passband containing fundamental and harmonic signal bands.
Figure 5:
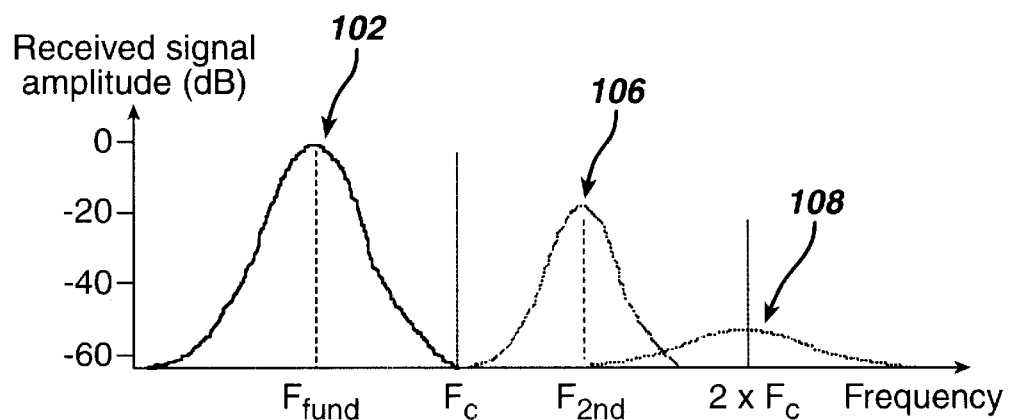
FIG. 5 illustrates the bands of signals remaining after summation of echoes received in response to the transmit bursts of FIGS. 3a and 3b.
Figure 6:
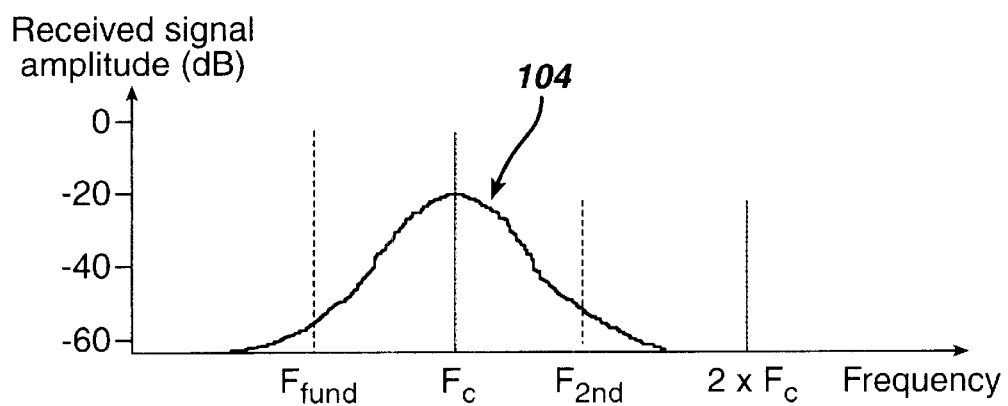
FIG. 6 illustrates the bands of signals remaining after subtraction of echoes received in response to the transmit bursts of FIGS. 3a and 3b.
Figure 3B:
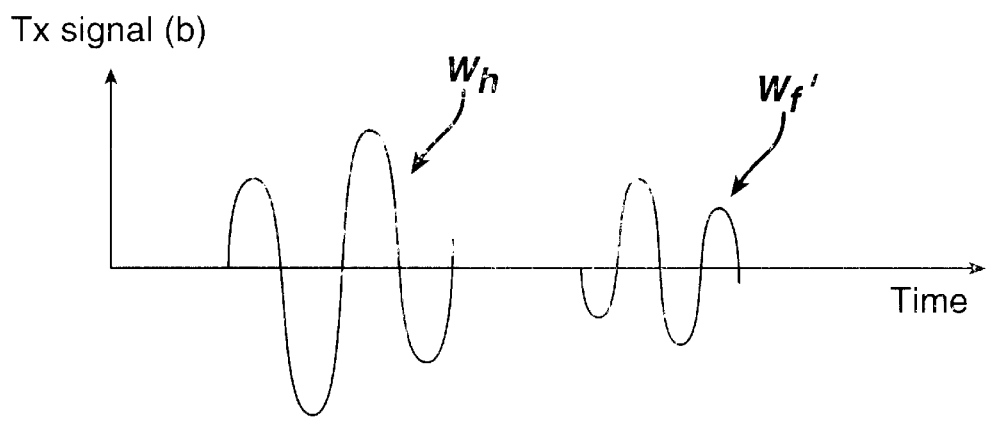
Figure 4:
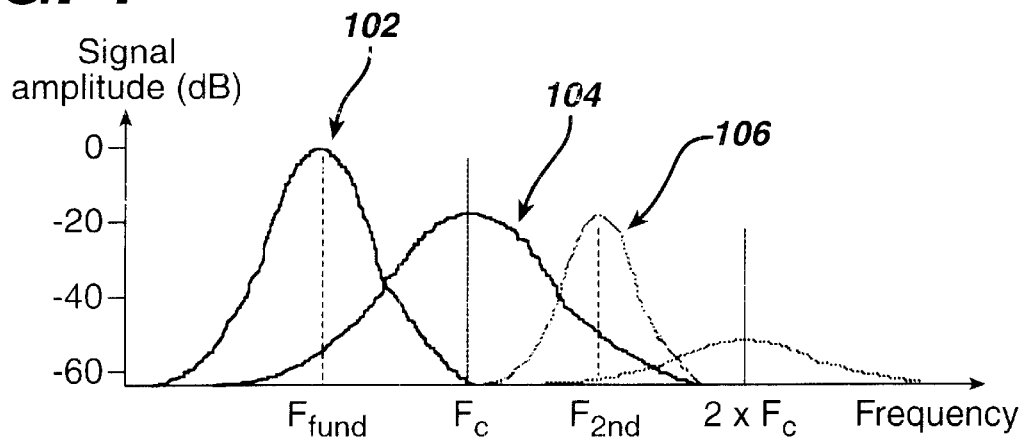
FIG. 4 illustrates the frequency content of signals received in response to the transmit bursts of FIGS. 3a and 3b.

The reason for inverting the conventional waveform $W_f{'}$ in the second of the two sequential bursts of FIG. 3b is demonstrated in FIGS. 5 and 6. FIG. 5 shows the frequency content of the signals after summing the received rf data from the sequential bursts, assuming no significant target movement between the bursts. Note that the fundamental component of the conventional waveform (band 104 in FIG. 4) which is differently modulated from burst to burst cancels out, as in pulse inversion harmonic separation, leaving the fundamental 102 and 2nd harmonic 106 bands of the THI waveform as the only significant components. This signal may then be processed as in normal (i.e., non pulse inversion) THI, by filtering out the fundamental signal in band 102 to generate a THI image using the signal content of band 106.

FIG. 6 shows the frequency content of the signals after subtracting the received rf data from the sequential bursts. Now only the odd components of the modulated conventional $W_f$ waveforms (i.e., the fundamental components of band 104) are preserved, because all of the signal arising from the THI waveform cancels. This signal can then be processed as in conventional fundamental imaging, using signal that utilizes the full bandwidth of the scanhead.

Figure 7A:
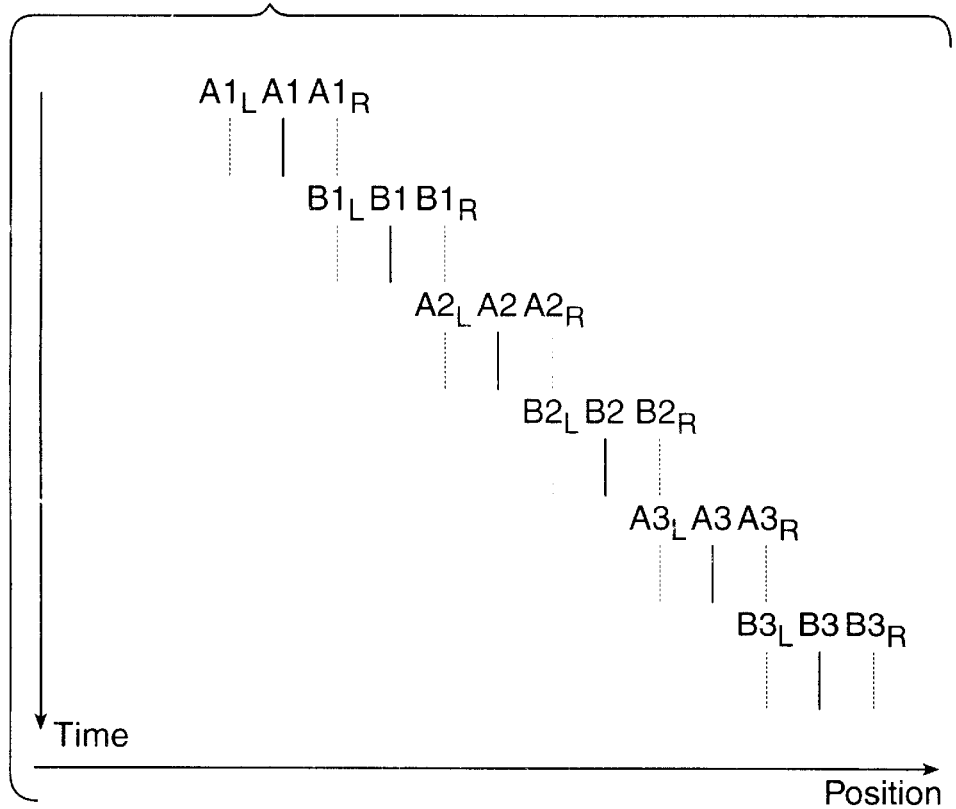
FIGS. 7a–7c illustrate an embodiment of the present invention which uses multiline reception and rf interpolation to form image lines from successive transmit bursts.
Figure 7B:
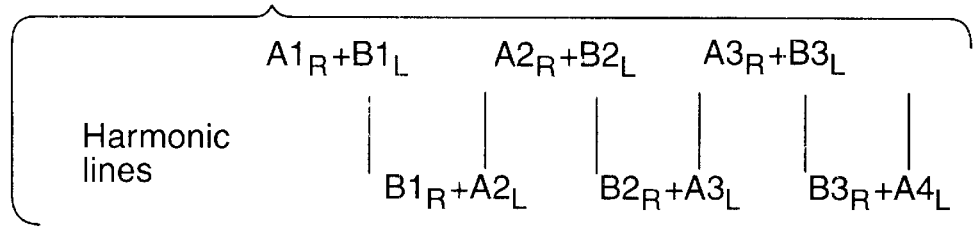
Figure 7C:
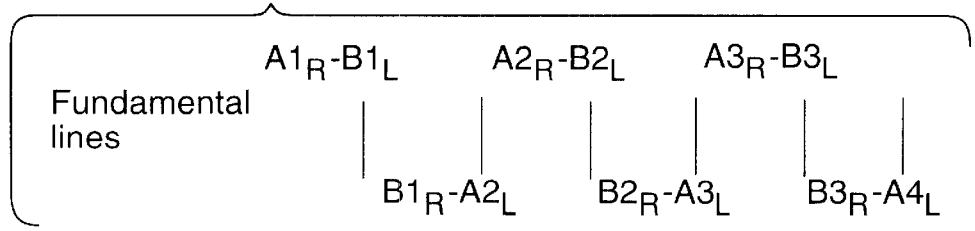

This two-burst technique still requires alternating pairs of transmit bursts and hence reduces the frame rate by a factor of two for a given line density. However, if the pairs of transmit bursts are displaced laterally by one line interval, combined multiline and rf interpolation techniques can be used to generate the sum and difference signals, as shown in FIGS. 7a–7c. In FIG. 7a the A1, A2 and A3 transmit bursts represent the timing and lateral spacing of dual waveform transmit bursts which are modulated in a first manner, e.g., as shown in FIG. 3a. As in the case of FIG. 2, multiline reception is employed to receive scanlines on either side of the center of the transmit beam. The interleaved transmit bursts B1, B2, B3 represent the timing and lateral spacing of dual waveform transmit burst which are modulated in a second manner, e.g., as shown in FIG. 3b. When the laterally aligned scanlines from the A and B transmit bursts are summed as shown in FIG. 7b, harmonic image lines are formed at the locations of the scanlines being combined, having the frequency content shown in FIG. 5. When the same scanline pairs are subtracted as shown in FIG. 7c, fundamental image lines are formed at the same spatial locations and with the frequency content shown in FIG. 6.

This approach has several advantages over the consecutive THI and conventional burst scheme shown in FIG. 2. First, for a given round-trip line spacing, the transmit line spacing is ½ the line spacing in FIG. 2 making it easier for transmit sampling requirements to be met. Second, the receive multilines are also ½ the distance from the transmit lines compared to FIG. 2. This means that more signal will be returned for a given transmit beam width, or that narrower transmit beam widths can be used. Third, the round-trip lines generated by the FIG. 2 technique are a mixture of common transmit and common receive lines, which show differing artifacts (such as susceptibility to motion as discussed above) and hence may generate "jail-bar" artifacts in the images. In the technique of FIG. 7, all of the round-trip lines are common receive lines.

One potential disadvantage with the approach of FIG. 7 is that the echoes from the two transmit bursts that are being summed or subtracted do not coincide exactly in space. This will result in reduced cancellation of the unwanted signals. That is, the conventional fundamental signal from harmonic imaging (see FIG. 5) or the THI signal from conventional imaging (see FIG. 6) may not fully cancel. However, it is likely that there will be sufficient overlap of the beams to provide sufficient cancellation for subsequent band-pass filtering to eliminate these unwanted signals.

For ultrasound systems that do not support multiline reception, the technique of FIG. 7 can be modified to form harmonic and fundamental image lines solely by rf interpolation. Under these circumstances each of the harmonic and fundamental lines in FIGS. 7b and 7c are formed from addition, or subtraction, of the rf data received from consecutive transmit bursts alternating between the A and B types, where only one scanline is received in response to each transmit burst and the receive scanline locations coincide with the corresponding transmit lines. This however has the disadvantage that the transmit/receive line density must satisfy the round-trip sampling requirements which avoid spatial aliasing, whereas in FIG. 7 only the sampling requirements for the transmit beam (which is typically broader) need be met.

Numerous display techniques may be employed using the simultaneously acquired harmonic and fundamental image data. As mentioned above, a single image can be formed which is a blend of both fundamental and harmonic image signals. An image may comprise solely or primarily fundamental signal data in the very near field where THI signals have not fully developed, may transition to solely harmonic signal data in the mid-field, and may transition again to solely or primarily fundamental signal data in the far field where harmonic signals are impacted by depth dependent attenuation. Alternately, a fundamental image and a harmonic image may be displayed side-by-side. Such a display would show the imaged region in both modes at the same time, and in time synchronization since the fundamental and harmonic signals are simultaneously acquired. The clinician can thus observe an image region in real time in both the harmonic mode and in the fundamental mode, thereby basing his diagnosis on image content which takes advantage of the characteristics of both modes of ultrasonic imaging.

Figure 8:
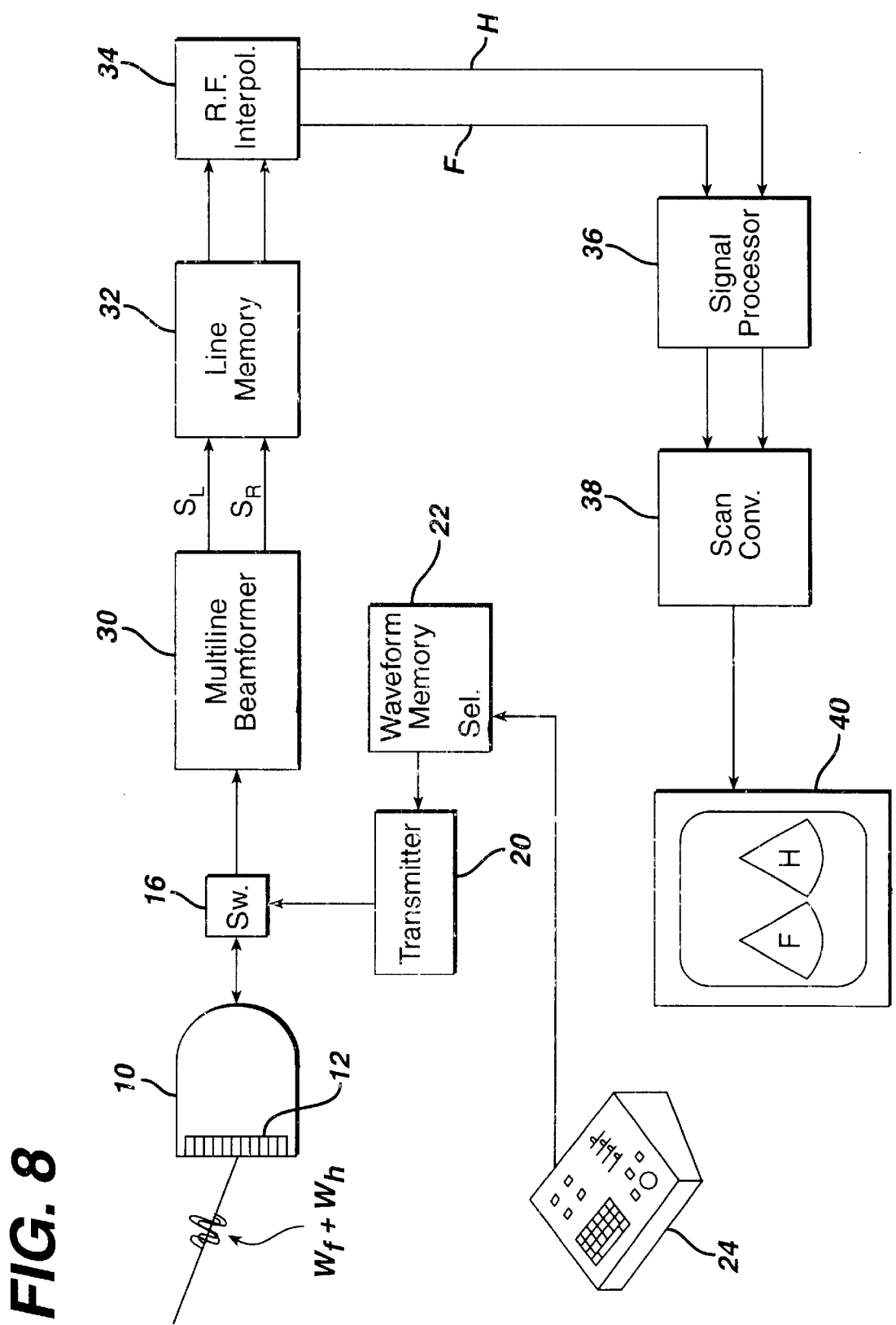
FIG. 8 illustrates an ultrasound system constructed in accordance with the principles of the present invention.

An ultrasound system which is configured to carry out the techniques of the present invention is shown in FIG. 8. A scanhead 10 has a transducer array 12 which steers and focuses a transmit beam which is a combination of fundamental and harmonic transmit waveform components $W_f + W_h$. The transmit waveform is stored in a waveform memory 22 and is selected by the clinician by operation of a user control 24. The selected transmit waveform is coupled to a transmitter 20 and applied to the elements of the transducer array at the appropriate times through a switch 16. During reception echoes received by the elements of the transducer array 12 are coupled by way of the switch 16 to a multiline beamformer 30. A multiline beamformer suitable for this application is described in U.S. patent application Ser. No. 09/746,165. The multiple scanlines $S_L$ and $S_R$ received in response to a composite transmit burst are stored in a line memory 32 until the scanlines needed to interpolate a desired image line have been acquired. The scanlines are coupled to an R.F. interpolator 34 which produces fundamental and harmonic image signals. These signals are processed by a signal processor 36 which may include filtering to remove any residual undesired signal components. The processed signals are coupled to a scan converter 38 which forms a harmonic image, a fundamental image, a blended harmonic/fundamental image, or both a fundamental and a harmonic image. Blended images may contain some regions of primarily fundamental image information, other regions of primarily harmonic image information, and regions which are a blend of both, as described in U.S. Pat. No. 6,283,919. This compounding of fundamental and harmonic image information will also reduce the speckle artifacts of the image. The ultrasonic image or images are then displayed on an image display 40. In the illustration the display 40 is shown displaying simultaneously acquired real time fundamental and harmonic images.

The present techniques may be used for harmonic imaging of contrast agents or for harmonic imaging of tissue in the absence of contrast agents. Contrast agents may be more distinctly imaged by using ratios or differences of the fundamental and harmonic signals to identify them, similar to the technique described in U.S. Pat. No. 5,526,816 which uses different frequency signals which are indicative of tissue and microbubble resonance.

What is claimed is:

1. A method for performing simultaneous ultrasonic fundamental and harmonic imaging comprising:
    transmitting an ultrasonic signal which includes a waveform component selected for fundamental imaging and a waveform component selected for harmonic imaging;
    receiving echoes in response to the transmitted ultrasonic signal;
    separating fundamental and harmonic echo components from the received echoes; and
    producing an image from at least one of the separated fundamental and harmonic echo components.

2. The method of claim 1, wherein producing comprises producing an image which is a blend of both fundamental and harmonic echo components.

3. The method of claim 1, wherein producing comprises producing a fundamental image and a harmonic image which are displayed simultaneously.

4. The method of claim 1, wherein the waveform component selected for harmonic imaging exhibits a greater amplitude in the transmitted signal than the waveform component selected for fundamental imaging.

5. A method for performing simultaneous ultrasonic fundamental and harmonic imaging comprising:
    transmitting an ultrasonic signal which includes a waveform component selected for fundamental imaging and a waveform component selected for harmonic imaging;
    receiving echoes in response to the transmitted ultrasonic signal;
    separating fundamental and harmonic echo components from the received echoes; and
    producing an image from at least one of the separated fundamental and harmonic echo components, further comprising:
        transmitting a second ultrasonic signal which includes a waveform component selected for harmonic imaging, and a waveform component selected for fundamental imaging which is modulated differently than the waveform component selected for fundamental imaging in the first-named ultrasonic signal;

receiving echoes in response to the second transmitted ultrasonic signal; and wherein separating comprises combining the echoes received from the transmitted ultrasonic signals.

6. The method of claim 5, wherein the echoes received from the transmitted ultrasonic signals are additively combined to separate harmonic echo components; and wherein the echoes received from the transmitted ultrasonic signals are subtractively combined to separate fundamental echo components.

7. The method of claim 1, wherein the waveform components are temporally coincident.

8. The method of claim 1, wherein the waveform components are sequential.

9. The method of claim 5, wherein the waveform components of each of the ultrasonic signals are temporally coincident.

10. The method of claim 5, wherein the waveform components of each of the ultrasonic signals are sequential.

11. An ultrasonic diagnostic imaging system which is capable of performing both fundamental and harmonic ultrasonic imaging comprising:
a transducer which transmits bursts including both fundamental waveform components and harmonic waveform components;
a multiline beamformer, coupled to the transducer, which produces multiple receive scanlines in response to a single transmit burst;
an rf interpolator, coupled to the multiline beamformer, which produces at least one of fundamental and harmonic signal information in response to received scanlines; and
a display which displays an image produced from signal information produced by the rf interpolator.

12. The ultrasonic diagnostic imaging system of claim 11, wherein the rf interpolator produces separated harmonic and fundamental signal information.

13. The ultrasonic diagnostic imaging system of claim 12, wherein the transducer transmits sequential bursts with differently modulated fundamental waveform components and similarly modulated harmonic waveform components.

14. The ultrasonic diagnostic imaging system of claim 13, wherein the rf interpolator produces separated harmonic and fundamental signal information by combining scanline echoes received from differently modulated transmit bursts.

15. An ultrasonic diagnostic imaging system which is capable of performing both fundamental and harmonic ultrasonic imaging comprising:
a transducer which transmits bursts including both fundamental waveform components and harmonic waveform components;
a multiline beamformer, coupled to the transducer, which produces multiple receive scanlines in response to a single transmit burst;
an rf interpolator, coupled to the multiline beamformer, which produces at least one of fundamental and harmonic signal information in response to received scanlines; and
a display which displays an image produced from signal information produced by the rf interpolator,
wherein the rf interpolator produce separated harmonic and fundamental signal information,
wherein the transducer transmits sequential bursts with differently modulated fundamental waveform components and similarly modulated harmonic waveform components,
wherein the rf interpolator produces separated harmonic and fundamental signal information by combining scanline echoes received from differently modulated transmit bursts, and
wherein the rf interpolator produces separated harmonic signal information by additively combining scanline echoes, and produces separated fundamental signal information by subtractively combining scanline echoes.

16. An ultrasonic diagnostic imaging system which is capable of performing both fundamental and harmonic ultrasonic imaging comprising:
a transducer which transmits bursts including both fundamental waveform components and harmonic waveform components;
a multiline beamformer, coupled to the transducer, which produces multiple receive scanlines in response to a single transmit burst;
an rf interpolator, coupled to the multiline beamformer, which produces at least one of fundamental and harmonic signal information in response to received scanlines; and
a display which displays an image produced from signal information produced by the rf interpolator,
wherein the display displays a fundamental image and a harmonic image concurrently.

17. The ultrasonic diagnostic imaging system of claim 16, wherein the fundamental and harmonic images comprise real time fundamental and harmonic images.

18. The ultrasonic diagnostic imaging system of claim 11, wherein the display comprises a display which displays an image which is a blend of fundamental and harmonic signal information produced by the rf interpolator.

19. The ultrasonic diagnostic imaging system of claim 18, wherein the image exhibits at least two of:
a region formed primarily from harmonic signal information;
a region formed primarily from fundamental signal information; and
a region formed approximately equally from harmonic and fundamental signal information.

20. The ultrasonic diagnostic imaging system of claim 11, wherein the transducer further scans a subject, and wherein the transmit bursts acquire echo information from a contrast agent in the subject.

21. An ultrasonic diagnostic imaging system which is capable of performing both fundamental and harmonic ultrasonic imaging comprising:
a transducer which transmits bursts including both fundamental waveform components and harmonic waveform components;
a multiline beamformer, coupled to the transducer, which produces multiple receive scanlines in response to a single transmit burst;
an rf interpolator, coupled to the multiline beamformer, which produces at least one of fundamental and harmonic signal information in response to received scanlines; and
a display which displays an image produced from signal information produced by the rf interpolator,
wherein the transducer further scans a subject, and wherein the transmit bursts acquire echo information from a contrast agent in the subject, and further comprising
a processor which acts to compare fundamental and harmonic signal information to identify the presence of a contrast agent.

22. The ultrasonic diagnostic imaging system of claim 21, wherein the processor acts to compute one of a ratio and a difference of fundamental and harmonic signal information.

23. The ultrasonic diagnostic imaging system of claim 11, wherein the transducer further scans a subject, and wherein the transmit bursts acquire echo information from the subject in the absence of a contrast agent.

24. The ultrasonic diagnostic imaging system of claim 14, further comprising a detector, and wherein detected harmonic and fundamental signal information is combined to reduce speckle.

25. A method of producing ultrasonic diagnostic imaging signals comprising:
   transmitting a first multicomponent waveform;
   receiving echoes in response to the first multicomponent waveform;
   transmitting a second multicomponent waveform having at least one component corresponding to a component of the first multicomponent waveform which exhibits a different phase modulation than the corresponding component;
   receiving echoes in response to the second multicomponent waveform; and
   combining the received echoes to produce ultrasonic imaging signals.

26. The method of claim 25, wherein combining comprises producing fundamental and harmonic ultrasonic imaging signals.

27. A method of producing ultrasonic diagnostic imaging signals comprising:
   transmitting a first multicomponent waveform;
   receiving echoes in response to the first multicomponent waveform;
   transmitting a second multicomponent waveform having at least one component corresponding to a component of the first multicomponent waveform which exhibits a different amplitude modulation than the corresponding component;
   receiving echoes in response to the second multicomponent waveform; and
   combining the received echoes to produce ultrasonic imaging signals.

28. The method of claim 27, wherein combining comprises producing fundamental and harmonic ultrasonic imaging signals.

* * * * *